(12) United States Patent
Keller

(10) Patent No.: US 9,326,837 B2
(45) Date of Patent: *May 3, 2016

(54) ARTICLE AND METHOD FOR CONTROLLING ORAL-ORIGINATED SYSTEMIC DISEASE

(71) Applicant: Duane C. Keller, St. Louis, MO (US)

(72) Inventor: Duane C. Keller, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/624,105

(22) Filed: Feb. 17, 2015

(65) Prior Publication Data

US 2015/0297331 A1    Oct. 22, 2015

Related U.S. Application Data

(63) Continuation of application No. 12/264,765, filed on Nov. 4, 2008, now Pat. No. 8,956,161.

(51) Int. Cl.
*A61C 19/06* (2006.01)
*A61K 8/04* (2006.01)
*A61K 8/22* (2006.01)
(Continued)

(52) U.S. Cl.
CPC ............ *A61C 19/063* (2013.01); *A61C 1/00* (2013.01); *A61C 1/0046* (2013.01); *A61C 9/0006* (2013.01); *A61C 17/20* (2013.01); *A61C 17/22* (2013.01); *A61C 19/066* (2013.01); *A61K 8/042* (2013.01); *A61K 8/22* (2013.01); *A61K 8/42* (2013.01); *A61Q 11/00* (2013.01); *A61K 2800/88* (2013.01); *A61K 2800/92* (2013.01)

(58) Field of Classification Search
CPC .... A61C 19/063; A61C 19/06; A61C 19/066; A61C 17/20; A61K 8/22; A61Q 11/00

USPC .............. 433/80–89, 215, 216, 229; 514/900, 514/902
See application file for complete search history.

(56) References Cited

U.S. PATENT DOCUMENTS 4,514,382 A    4/1985    Gaffar et al.
4,568,535 A    2/1986    Loesche
(Continued)

OTHER PUBLICATIONS

Feres et. al. Antibiotics in the Treatment of Periodontal Diseases: Microbiological Basis and Clinical Applications. Ann Roy Australas Coll Dent Surg, Jun. 2008; 19:37-44; p. 40, col. 2, para 4; p. 41, col. 1, para 1.

(Continued)

*Primary Examiner* — Edward Moran
(74) *Attorney, Agent, or Firm* — Polster Lieder

(57) ABSTRACT

Methods for treating systemic disease in oral biofilms having a facultative anaerobic bacteria pathogen present including providing a periodontal medicament delivery tray having a seal against a patient's adjacent gums containing the oral biofilms with the systemic disease, said seal formed so as to have no contact with teeth, applying to the gingival tissue (sulcus or periodontal pocket) a biofilm penetrating antimicrobial agent, removing the imbedded anaerobic bacteria from the gingival tissue following at least one applying of the antimicrobial agent to the gingival tissue; repeatedly administering colloidal hydrogen peroxide gel to the gingival tissue following the removing of imbedded anaerobic bacteria; and following each administering cleaning the gingival tissue with a cleaning agent directly following the administering of the colloidal hydrogen peroxide gel for modifying the environment from anaerobic to aerobic.

20 Claims, 6 Drawing Sheets

(51) Int. Cl.
*A61Q 11/00* (2006.01)
*A61C 1/00* (2006.01)
*A61C 9/00* (2006.01)
*A61C 17/20* (2006.01)
*A61C 17/22* (2006.01)
*A61K 8/42* (2006.01)

(56) References Cited

U.S. PATENT DOCUMENTS

| | | |
|---|---|---|
| 4,569,837 A | 2/1986 | Suzuki et al. |
| 4,670,252 A | 6/1987 | Sampathkumar |
| 4,701,320 A | 10/1987 | Hasegawa et al. |
| 4,751,051 A | 6/1988 | Thompson et al. |
| 4,819,158 A | 4/1989 | Miyashita |
| 4,842,846 A | 6/1989 | Nakano |
| 4,892,736 A | 1/1990 | Goodson |
| 4,906,670 A | 3/1990 | Higashi et al. |
| 4,916,193 A | 4/1990 | Tang et al. |
| 4,933,182 A | 6/1990 | Higashi et al. |
| 4,963,347 A | 10/1990 | Humphries et al. |
| 4,966,774 A | 10/1990 | Nakano et al. |
| 4,975,271 A | 12/1990 | Dunn et al. |
| 4,980,152 A | 12/1990 | Frazier et al. |
| 4,985,235 A | 1/1991 | Kligman |
| 4,990,329 A | 2/1991 | Sampathkumar |
| 5,032,384 A | 7/1991 | Yeh et al. |
| 5,057,497 A | 10/1991 | Calam et al. |
| 5,087,451 A | 2/1992 | Wilson et al. |
| 5,110,583 A | 5/1992 | Sampathkumar |
| 5,129,824 A | 7/1992 | Keller |
| 5,160,737 A | 11/1992 | Friedman et al. |
| 5,176,901 A | 1/1993 | Gallopo et al. |
| 5,188,817 A | 2/1993 | Ozick |
| 5,217,710 A | 6/1993 | Williams et al. |
| 5,240,710 A | 8/1993 | Bar-Shalom et al. |
| 5,277,908 A | 1/1994 | Beckman et al. |
| 5,330,357 A | 7/1994 | Keller |
| 5,340,566 A | 8/1994 | Curtis et al. |
| 5,372,802 A | 12/1994 | Barrows et al. |
| 5,374,418 A | 12/1994 | Oshino et al. |
| 5,409,703 A | 4/1995 | McAnalley et al. |
| 5,419,703 A | 5/1995 | Warrin et al. |
| 5,438,076 A | 8/1995 | Friedman et al. |
| 5,472,684 A | 12/1995 | Nabi et al. |
| 5,599,553 A | 2/1997 | Chung |
| 5,605,676 A | 2/1997 | Gaffar et al. |
| 5,607,681 A | 3/1997 | Galley et al. |
| 5,607,686 A | 3/1997 | Totakura et al. |
| 5,616,313 A | 4/1997 | Williams et al. |
| 5,632,972 A | 5/1997 | Williams et al. |
| 5,639,795 A | 6/1997 | Friedman et al. |
| 5,648,399 A | 7/1997 | Friedman et al. |
| 5,701,320 A | 12/1997 | Sugiyama et al. |
| 5,709,873 A | 1/1998 | Bar-Shalom et al. |
| 5,730,995 A | 3/1998 | Shirono et al. |
| 5,800,803 A | 9/1998 | Mirajkar et al. |
| 5,817,294 A | 10/1998 | Arnold |
| 5,820,841 A | 10/1998 | Chen et al. |
| 5,827,503 A | 10/1998 | Schwabe |
| 5,885,553 A | 3/1999 | Michael |
| 5,906,811 A | 5/1999 | Hersh |
| 5,908,613 A | 6/1999 | Bozzacco |
| 5,908,614 A | 6/1999 | Montgomery |
| 5,928,187 A | 7/1999 | Glukhov et al. |
| 5,939,080 A | 8/1999 | Michael et al. |
| 5,998,487 A | 12/1999 | Brahms et al. |
| 6,049,002 A | 4/2000 | Mattila et al. |
| 6,080,712 A | 6/2000 | Revell et al. |
| 6,153,210 A | 11/2000 | Roberts et al. |
| 6,200,550 B1 | 3/2001 | Masterson et al. |
| 6,228,347 B1 | 5/2001 | Hersh |
| 6,228,354 B1 | 5/2001 | Jeng |
| 6,232,340 B1 | 5/2001 | Zhang et al. |
| 6,247,930 B1 | 6/2001 | Chiang et al. |
| 6,290,934 B1 | 9/2001 | Kramer et al. |
| 6,314,960 B1 | 11/2001 | Vines |
| 6,325,991 B1 | 12/2001 | Draheim |
| 6,409,992 B1 | 6/2002 | Kleinberg et al. |
| 6,416,745 B1 | 7/2002 | Markowitz et al. |
| 6,610,274 B1 | 8/2003 | Gardner |
| 6,682,722 B2 | 1/2004 | Majetti et al. |
| 6,685,921 B2 | 2/2004 | Lawlor |
| 6,692,727 B1 | 2/2004 | Yue et al. |
| 6,764,690 B2 | 7/2004 | Ahola et al. |
| 6,776,979 B2 | 8/2004 | Frager et al. |
| 6,929,790 B2 | 8/2005 | Kleinberg et al. |
| 6,966,773 B2 * | 11/2005 | Keller ............... A61C 19/066 433/215 |
| 7,018,622 B2 | 3/2006 | Goodhart et al. |
| 7,025,950 B2 | 4/2006 | Majeti et al. |
| 7,094,431 B2 | 8/2006 | Peshoff |
| 7,150,884 B1 | 12/2006 | Hilgren et al. |
| 7,190,884 B2 | 3/2007 | Fujiwara et al. |
| 2004/0019110 A1 | 1/2004 | Van Dyke et al. |
| 2004/0091432 A1 | 5/2004 | Dulin |
| 2004/0097432 A1 | 5/2004 | Roh-Schmidt et al. |
| 2004/0126440 A1 | 7/2004 | Frager et al. |
| 2004/0265396 A1 | 12/2004 | Peshoff |
| 2005/0203587 A1 | 9/2005 | Liebergesell |
| 2006/0034782 A1 | 2/2006 | Brown et al. |
| 2006/0036194 A1 | 2/2006 | Schultheiss et al. |
| 2006/0093561 A1 | 5/2006 | Kennedy |
| 2006/0182813 A1 | 8/2006 | Holladay |
| 2006/0257331 A1 | 11/2006 | Dulin |
| 2006/0271148 A1 | 11/2006 | Liebergesell et al. |
| 2007/0122490 A1 | 5/2007 | Peshoff |
| 2009/0092947 A1 * | 4/2009 | Cao ..................... A61C 1/0046 433/215 |

OTHER PUBLICATIONS

Kolenbrander et al. Communication among Oral Bacteria. Microbiol. Mol. Biol. Rev. 2002, 66(3): 486-505; p. 486, col. 2, para 3; p. 487, col. 1 para 1; p. 488, col. 2, para 1; p. 489, col. 1, para 1; p. 497, col. 1, para 1-2.

* cited by examiner

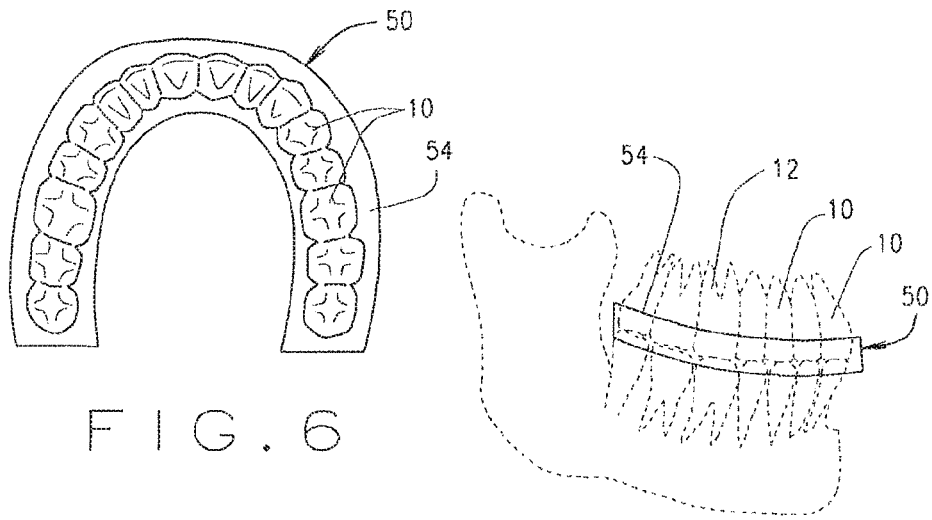
FIG. 6
FIG. 7
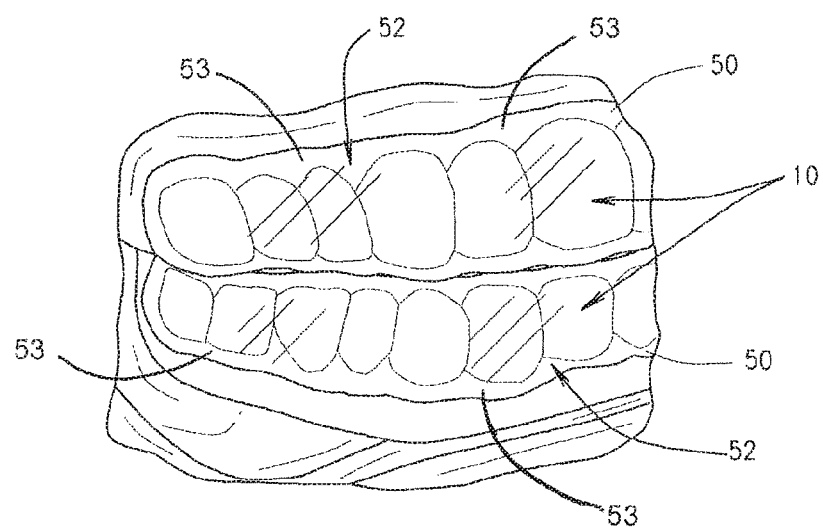
FIG. 8

ARTICLE AND METHOD FOR CONTROLLING ORAL-ORIGINATED SYSTEMIC DISEASE

CROSS-REFERENCE TO RELATED APPLICATIONS

This application is a continuation of U.S. patent application Ser. No. 12/264,765 filed on Nov. 4, 2008. The disclosure of the above application is incorporated herein by reference.

FIELD

The present disclosure relates to treatment of periodontal disease and, more specifically, to systems and methods for treating oral bacteria that result in systemic disease in a patient.

BACKGROUND

The statements in this section merely provide background information related to the present disclosure and may not constitute prior art.

Medical research has demonstrated a significant source of systemic disease is related to specific oral bacteria, with special emphasis on certain gram negative anaerobic bacteria that have been found associated with a variety of systemic inflammatory responses and appear to originate only in periodontal pockets and enter the bloodstream through a close proximity to the host circulatory system.

There are very few regions of the body which can readily be rendered conducive to the growth of anaerobic bacteria. Deeper periodontal pockets are one region that readily demonstrates infections that are predominantly anaerobic, with gram-negative bacteria being the most common isolates. The anatomic closeness of these biofilm periopathogens to the bloodstream can facilitate bacteremia and systemic spread of bacterial products, components, and immunocomplexes (antigen/antibody reactions, chemokines and cytokines).

It has been found that these oral periopathogens can become systemic. Research has demonstrated that bacteremia was observed in 100% of the patients after dental extraction and in 70% after dental scaling. Mastication on infected gum tissues increases systemic bacterial endotoxins levels four-fold. Simple oral hygiene procedures, such as brushing of the teeth, can increase the prevalence of bacteremia from 17 to 40%. Research has also demonstrated that the dissemination of oral microorganisms into the bloodstream is common. In fact, it has been found that within less than 1 minute after an oral procedure, organisms from an infected site can reach the heart, lungs, and peripheral blood capillary system of a patient. These periopathogens can cause host injury (exotoxins and toxic bacterial products), inflammation (immune system—antigen/antibody reactions) and infections (bacteremia) in a person. Periodontitis may affect the host's susceptibility to systemic disease in three ways: by shared risk factors, by subgingival biofilms acting as reservoirs of bacteria, and through the periodontium acting as a reservoir of inflammatory mediators.

It has also been found that controlling these periopathogens in the mouth decreases systemic responses. Studies have evaluated periodontitis and C-reactive protein (CRP) levels in patients. For example, one study evaluated three groups: (1) an untreated control group of 24 subjects; (2) a group of 21 subjects with a standard regimen of periodontal therapy (SPT), consisting of subgingival mechanical instrumentation; and (3) a group of 20 subjects who had an intensive course of periodontal treatment (IPT), consisting of SPT with adjunctive local delivery of minocycline-HCl (Arestin®, Orapharma, Warminster, Pa., USA). The results of this study in both treatment groups identified a considerable reduction of periodontal lesions after therapy [60±27 (P<0.0001, N=21) and 60±23 (P<0.0001, N=20) mean differences tested by t test, respectively]. No changes were observed in the untreated controls. Similar results were found in the IL-6 markers. The report of that study concluded that periodontitis causes moderate systemic inflammation in systemically healthy patients because reducing the periodontal disease resulted in a reduction in the systemic inflammatory markers.

Periodontitis is an infection that can stimulate the liver to produce C-reactive protein (CRP) (a marker of inflammation), which in turn will form deposits on injured blood vessels. CRP binds to cells that are damaged and fixes complement, which activates phagocytes, including neutrophils. These cells release nitric oxide, thereby contributing to atheroma formation. It has been found that patients with adult periodontitis have higher levels of CRP and haptoglobin than subjects without periodontitis. Both CRP and haptoglobin levels decline significantly after periodontal therapy. Additionally, in another study of 153 systemically healthy subjects consisted of 108 untreated periodontitis patients and 45 control subjects, the mean plasma CRP levels were higher in the periodontitis patients. Patients with severe periodontitis had significantly higher CRP levels than mild-periodontitis patients, and both had significantly higher levels than the controls. Another recent study evaluated the relationship of cardiovascular disease and CRP into three groups of adults: i) had neither periodontal nor cardiovascular disease, ii) had only one of these two diseases, and iii) had both of two diseases. In those with both heart disease and periodontal disease, the mean level of CRP (8.7 g/ml) was significantly different from that (1.14 g/ml) in controls with neither disease. It was also shown in that study that treatment of the periodontal disease caused a 65% reduction in the level of CRP within 3 months of treatment.

However, current methods to treat periodontal disease and the resulting effects thereof suffer from a number of significant drawbacks and are often ineffective in addressing the systemic effects of periodontal originated disease. Many of the systemic biomarkers decrease following conventional oral disinfection, but these biomarker decreases are short lived and return to abnormal elevated pre-treatment levels. The inventor of the present methods and systems has identified a significant need and benefit to many patients in developing new procedures and systems that address the systemic effects of periodontal originated diseases.

SUMMARY

The inventor hereof has succeeded at designing methods and systems for treatment of periodontal disease in patients that eliminate 99+% of the periopathogens within 12 to 17 days of treatment, and the treatment method becomes modified into the homecare method and is able to maintain these improvements long-term. The method and system thus provides an improved effectiveness in reducing and/or eliminating resulting systemic disease resulting therefrom. These include the application of a treatment plan or administration of steps to a patient suffering from periodontal disease for managing the most virulent anaerobic bacteria by altering the environment from one conducive to disease (anaerobic) to one that is conducive to health (aerobic). As described herein, various methods and systems as described herein address the pathogens in a synergistic approach that provide steps that collectively have an unknown or unexpected benefit over the expected results of each of the separate or individual steps. Generally, at least some of the methods as described herein can be adapted for self-administration by the patient in a manner such that the oral environment can be permanently altered from anaerobic aerobic, thereby not only eliminating the periopathogens but also eliminating the environment in which they can return. In a like manner, other medications can be used to modify the environment from one of disease to one conducive to health. These can be monitored over time and adjustments made as deemed necessary to promote a healthy environment.

According to one aspect, a method of treating oral biofilms includes applying an antimicrobial agent to subgingival biofilm and gingival tissue associated with the subgingival biofilm, altering an environment associated with the subgingival biofilm from anaerobic to aerobic and modifying a protein or amino acid substratum associated with the subgingival biofilm in a substantially irreversible manner. The method also includes removing imbedded aerobic and anaerobic bacteria from the gingival tissue following at least one application of the antimicrobial agent and administering colloidal hydrogen peroxide gel to a periodontal pocket associated with the subgingival biofilm and the gingival tissue in conjunction with or following the removing of imbedded anaerobic bacteria for facilitating further removal of imbedded anaerobic bacteria. The method further includes cleaning the gingival tissue with a cleaning agent directly following the administering of the colloidal hydrogen peroxide gel.

According to another aspect, a method of treating gingival tissue infected with virulent bacteria includes the steps of applying to the gingival tissue an antimicrobial agent that is delivered and maintained in a manner that controls, suspends or eradicates the function of the virulent bacteria such as removing imbedded anaerobic bacteria from the gingival tissue following at least one application of the antimicrobial agent to the gingival tissue; administering colloidal hydrogen peroxide gel to the gingival tissue for further removing of imbedded anaerobic bacteria; and cleaning the gingival tissue with a cleaning agent directly following the administering of the colloidal hydrogen peroxide gel. According to some embodiments, it is now possible to recognize the different bacteria or other micro-organisms in various regions of the periodontium by PCR-DNA analysis and by other means. Specific antimicrobial agents that are best able to manage the micro-organisms in the various regions can be site-specifically delivered to the various regions to facilitate optimal microbial control and long-term maintenance.

Further aspects of the present disclosure will be in part apparent and in part pointed out below. It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

FIG. 6 is a top plan view of a periodontal medicament delivery tray suitable for use with one or more embodiments of the present disclosure.

FIG. 7 is a side elevational view of a periodontal medicament delivery tray as worn by a patient for use in one or more embodiments of the treatments of the present disclosure.

FIG. 8 is a side elevational view of upper and lower periodontal medicament delivery trays as worn by a patient for simultaneous treatment of both the upper and lower teeth and associated marginal gingiva according to some embodiments.

It should be understood that throughout the drawings, corresponding reference numerals indicate like or corresponding parts and features.

DETAILED DESCRIPTION

The following description is merely exemplary in nature and is not intended to limit the present disclosure or the disclosure's applications or uses. Before turning to the figures and the various exemplary embodiments illustrated therein, a detailed overview of various embodiments and aspects is provided for purposes of breadth of scope, context, clarity, and completeness.

Periodontal disease has been found to be caused by planktonic bacteria or bacterium and/or micro-organisms living in a biofilm. The most virulent of these bacteria have inherent properties that include being gram negative-obligate anaerobes. These gram negative obligate anaerobic bacteria live in a biofilm in the deeper periodontal pockets are therefore harder to reach or eliminate by conventional means. The bacterial biofilm matrix composed of lipopolysaccharides, exopolysaccharides and other surface products as well as the endotoxins, exotoxins and other bacterial products cause signification immune system responses. In addition, these gram negative-obligate anaerobes have been found to invade the tissues causing localized and systemic inflammatory responses and to invade the individual cells and are then impervious the host immune system. The anaerobes as part of a biofilm are almost impervious to conventional treatments. Other micro-organisms, some of which may not yet be discovered, can be impervious to existing treatment modalities and can cause local and systemic effects.

Figure 1:
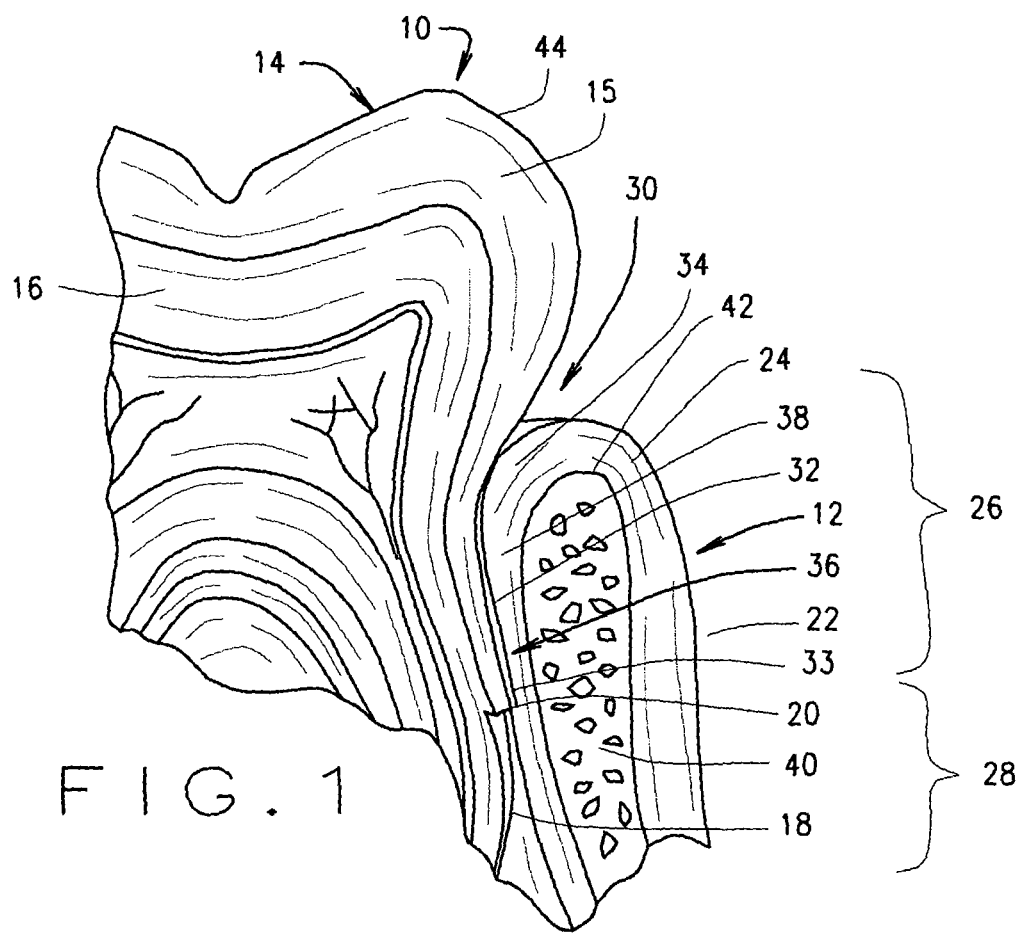
FIG. 1 is a cross-sectional view of a healthy tooth and gingival tissue.
Figure 2A:
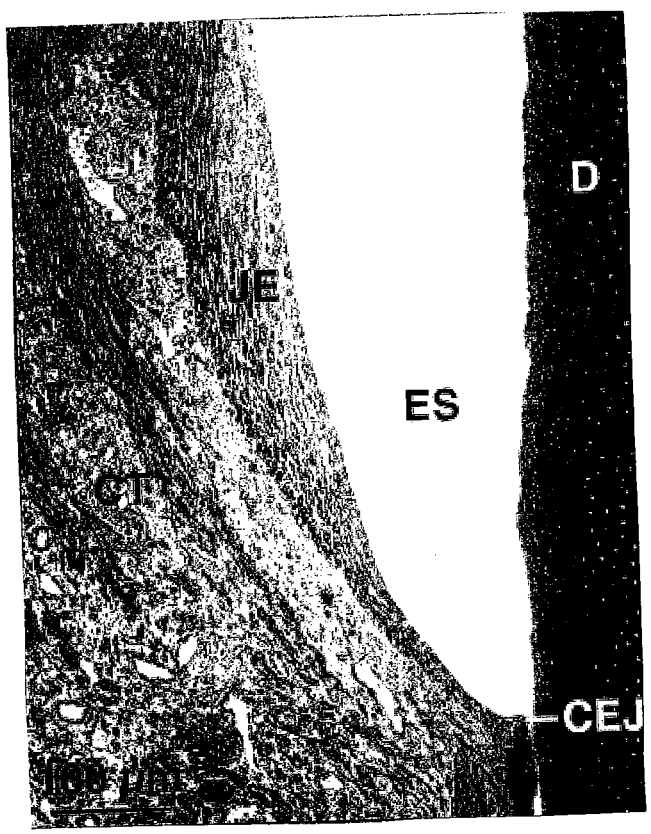
FIG. 2A is a cross-sectional close-up photographic image of a marginal gingiva and tooth structure including a cementoenamel junction.
Figure 2B:
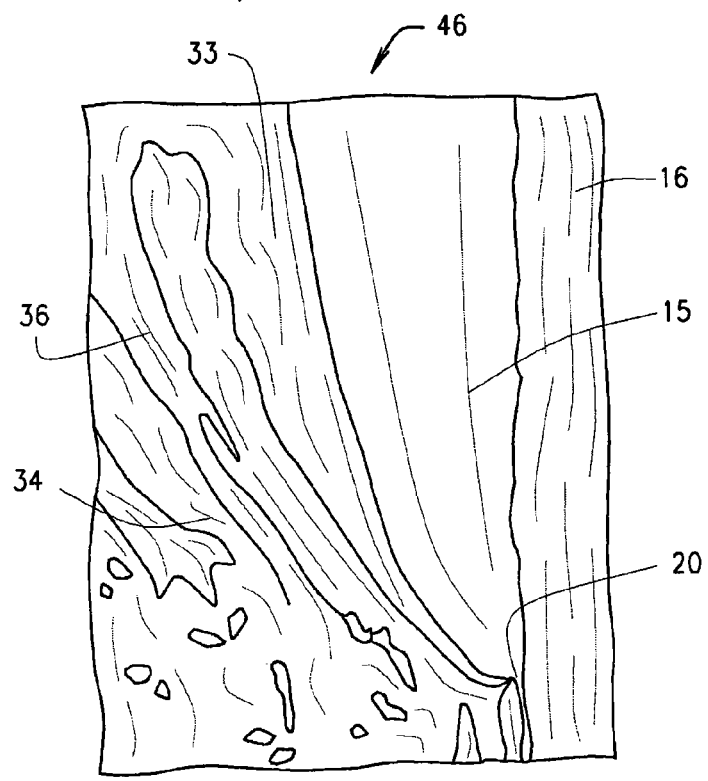
FIG. 2B is a line drawing representation of the photographic image of FIG. 2A.
Figure 3A:
FIG. 3A is a close-up side photographic image of a tooth and associated marginal gingiva.
Figure 3B:
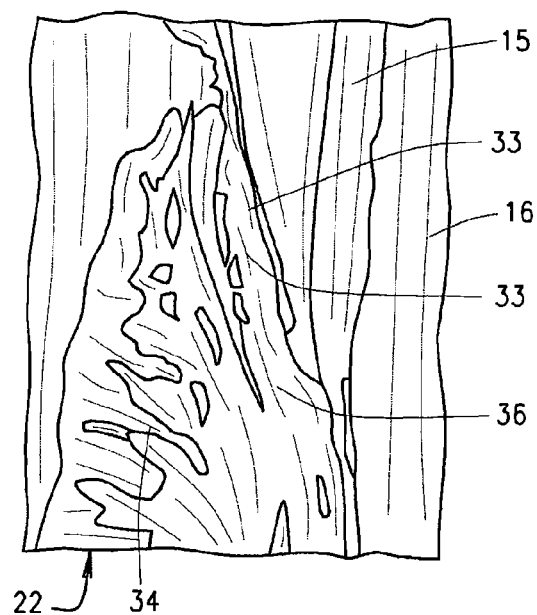
FIG. 3B is a line drawing representation of the photographic image of FIG. 3A.
Figure 4A:
FIG. 4A is another close-up side photographic image of a tooth and associated marginal gingiva.
Figure 4B:
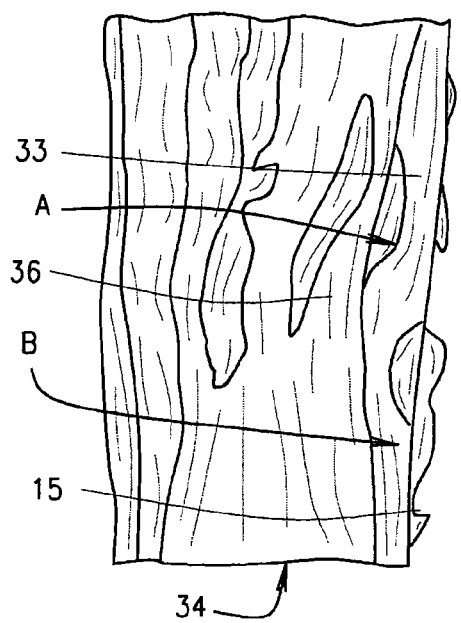
FIG. 4B is a line drawing representation of the photographic image of FIG. 3A.
Figure 5A:
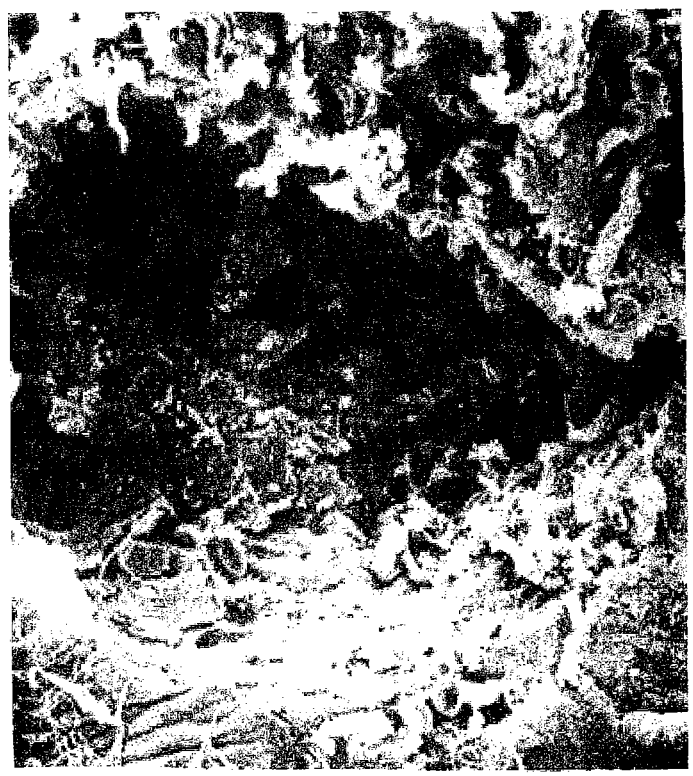
FIG. 5A is a photographic microscopic image of an ulcer in a periodontal pocket.
Figure 5B:
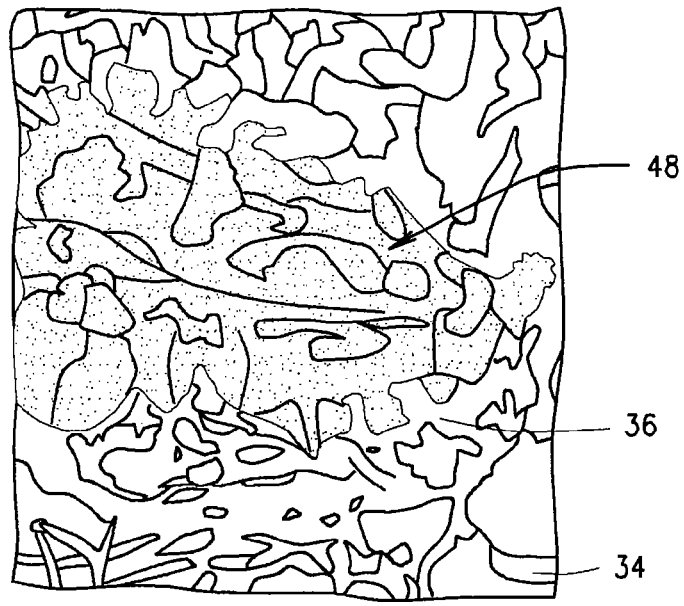
FIG. 5B is a line drawing representation of the photographic image of FIG. 5A.

FIG. 1 shows a healthy tooth 10 with surrounding gum 12. The tooth 10 includes a crown 14 having enamel 15, an inner composition of dentine 16 that forms the root of the tooth 10, and cementum 18 that covers the outer surface of the lower portions of the tooth 10 below the enamel 15. A cementoenamel junction (CEJ) 20 is defined as the intersection of the lower end of the enamel 15 and the start of the cementum 18. As shown, the gum 12 includes gingiva 22 that has gingival tissue 24 having a portion referred to as marginal gingiva tissue 26, and attached gingiva tissue 24, the two portions generally being separated by the CEJ 20. The gum 12 forms a gingival sulcus 30 at the intersection with the tooth 10. An epithelium 32 covers the lower portions of the enamel 15 above the CEJ 20 such that the cementum 18 is not exposed in a healthy tooth 10 as shown. Connective tissue 34 of the gingiva tissue 28 is adjacent to the epithelium 32 (this portion referred to as the junctional epithelium 33) and includes a bed of capillaries, hereinafter referred to as a capillary bed 36, and alveolar fibers 38. An alveolar bone 40 has an alveolar crest 42 that extends nearly to the CEJ 20 to form a deep socket (not shown) for the tooth 10. Biofilm 44 generally forms to coat the outer surface of the enamel 15. FIGS. 2A and 2B illustrates a close-up of an environment 46 about the CEJ 20 including the location of the junctional epithelium 33 between the enamel 15 and the connective tissue 34 that includes the capillary bed 36.

FIGS. 3A and 3B and 4A and 4B illustrate environment 46 in additional detail. From these detailed illustrations, that where epithelium 32 exists, as shown at "A" in FIG. 3B, there is only 1 or 2 cells separating the interface with the outer surfaces of the tooth 10 that can be exposed when the gingival sulcus 30 widens during infection. When the bacteria proliferate in this region the tissue is modified so there is no epithelium 32 present, shown at "B" in FIGS. 4A and 4B. The exposure of the underlying connective tissue 34 and capillary system 36 in direct contact or at least very close proximity of any pathogens present in the gingival sulcus 30 or, a periodontal pocket (not shown) associated therewith, provides access to the host circulatory system and thus systemic involvement is possible.

While not shown in the figures, in a diseased tooth 10 such as with one having an inflammation from periodontal disease, the junctional epithelium 32 moves apically (or toward the apex of the root), exposes the cementum 18 and enlarges the sulcus 30 thereby creating a pocket (not shown). Facultative anaerobes modify this environment 46 from one with minimal oxygen to an anaerobic environment conducive to development of virulent anaerobic periopathogens. An ulcer 48, such as shown under magnification in FIGS. 4A and 4B, can form in the periodontal pocket. As can be seen in this illustration, the ulcer 48 of the periodontal pocket can be directly adjacent to, and/or in contact with the capillary bed 36 of the connective tissue 34. As the inflammation spreads, the alveolar bone 40 is destroyed. This increases the mobility of the tooth 10 and can lead to loss of the tooth 10. Additionally, this enlarging reservoir (enlarged sulcus 30 and pocket) serves as a source of bacteria, bacterial products and host inflammatory responses that can become systemically involved via the close proximity to the host bloodstream.

In one embodiment, a method of treating gingival tissue, biofilm, such as may be infected with a periodontal disease, includes applying to the subgingival biofilm and/or gingival tissue an antimicrobial agent. For example, an antimicrobial agent that is capable of modifying the environment from an anaerobic situation to an aerobic one that can address the removing of imbedded anaerobic bacteria from the gingival tissue. The method can also include administering colloidal hydrogen peroxide gel to the gingival tissue for aiding in altering the environment from anaerobic to aerobic and thereby also addressing the imbedded anaerobic bacteria; and cleaning the gingival tissue with a cleaning agent directly following the administering of the colloidal hydrogen peroxide gel or other agents that may facilitate the antimicrobial or cleansing process. Specific antimicrobial agents that can best control specific biofilm bacteria can be applied to those regions where the specific microbes are found so as to best control the pathogen population. These site-specific medications can be modified as alterations in the biofilm matrix are determined by PCR-DNA analysis or by other means.

The method provides for the application or delivery of an antimicrobial agent, such as hydrogen peroxide by way of example, which can be delivered into the periodontal pocket and maintained in the pocket for a prescribed period of time sufficient to kill the periopathogens and to alter the environment from one conducive to disease (anaerobic) to one conducive to health (aerobic). In some embodiments, such antimicrobial agent is applied using a periodontal medicament delivery tray available to the patient or as procured during the first step, where applicable. Additionally, where an acute case is diagnosed, the application of the antimicrobial agent also follows the modification of the environment as provided in the altering process. Examples of currently known antimicrobial agents suitable for use and include Actisite, Atridox, Periochip, Arestin, Perio Tray™/colloidal hydrogen peroxide, Electrolyzed water, Alcohol, Iodine, and Hydrogen Peroxide.

As noted, the antimicrobial agents can be modified and/or customized in the biofilm matrix by PCR-DNA analysis or by other means. For example, during either an initial diagnosis procedure of a patient or where all or a portion of an affective region fails to favorably respond to a general broad-spectrum or another antimicrobial agent, a sample of the bacteria within the periodontal pocket can be obtained and forwarded to a lab for determining the particular pathogens. A sample can be taken from an attending medical practitioner by using any suitable means, including, by way of example, a paper point inserted into the periodontal pocket to be tested. After the diagnostic procedure is completed and the particular bacteria present in the periodontal pocket is determined, the antimicrobial agent is selected or customized, such as by creation of a blend or cocktail of agents or medicaments, for specifically controlling the determined bacteria. Such a process can be initiated at the beginning of a treatment as described herein, or can be performed during or with one or more of the other processes to aid in the overall treatment of the patient.

Referring to FIGS. 6, 7 and 8, a form-fitted flexible periodontal medicament delivery tray 50, is adapted for applying one or more of the medicaments 52 described in the various methods in accordance with various embodiments. More specifically, tray 50 is of a suitable soft plastic elastomeric or other suitable material which is molded in place to the patient's teeth so as to form a dental arch recess 54 which conforms closely to a patient's teeth and which firmly and closely fits in place on the patient's teeth. Tray 50 is shown to be a full arch tray, but those skilled in the art will recognize that a partial arch tray or a dual arch tray may be used, if desired.

In some embodiments, the patient can deliver the antimicrobial agent or agents to continue to manage the affected environment to kill or continue to kill the obligate and facultative anaerobes and/or prevent their formation in a general or a site specific manner. The application of the antimicrobial agent(s) or other medicaments beneficial to health can be provided as a long term treatment of which the patient self-applies at home. It can also be extended as needed to control any chronic aspects of the periodontal disease and to maintain an environment conducive to health that is aerobic and further inhibits the growth and re-growth of anaerobic bacteria.

The applied antimicrobial agent can be any antimicrobial agent that is suitable for managing the microorganisms and for maintaining a tissue environment that is conducive to health. This can be a medicament that is aerobic and inhibits the growth and re-growth of anaerobic bacteria or any other medicament conducive to a favorable and healthy situation. For example, this can include, but is not limited to hydrogen peroxide. Of course, it should be understood that the application of the antimicrobial agent can be a single application or can be multiple applications that can be generally delivered or site specifically delivered that are repeated more than once and can, in some embodiments, be repeated on a periodic basis. Additionally, such application of the antimicrobial agent can be provided several times each day or otherwise adjusted to the frequency as may be directed or performed by a dentist or health care professional.

It should be noted that the application of the antimicrobial agent can be performed in any suitable manner. In one embodiment, a tray adapted for directly applying a medicament to the gums about the teeth, the gingival tissue, is used. For example, the antimicrobial agent can be filled or at least partially filled into a cavity of periodontal medicament delivery tray. The tray can then be attached or applied to the gums and about the associated teeth for application of the medicament to the area to be treated. Additionally, as shown in FIG. 6, only one of the upper or lower teeth and associated gingival tissue can be treated or, as shown in FIG. 7, both the upper and lower teeth and associated gingival tissue can be treated simultaneously.

Following or during a portion of application of the antimicrobial agent and/or the modification of a protein or amino acid substratum associated with the subgingival biofilm and/or the environment, the method provides for the removal of imbedded anaerobic bacteria from the gum and/or affected connective tissue. Certain of the oral bacteria possess the capability of host cell invasion directly and cause the host cells to act in ways different from normal non-infected cells. These abnormal cells must be removed by any suitable procedure including surgery such as electro-surgery, scaling and root planning laser surgery or conventional "cold steel" surgery or any other means available for removing imbedded micro-organisms from the host cells/gum tissue. This process removes the imbedded pathogenic bacteria that have the potential to invade the host cells of the host tissue. The surgical removal is often required as these imbedded pathogenic bacteria are often impervious to most other treatment methods. While such pathogenic bacteria are controlled and/or killed in the procedures of applying an antimicrobial agent, altering the environment, and/or modifying a protein or amino acid substratum, the removal of the imbedded pathogenic bacteria is performed for providing a healthy and clean environment. Such removal can be by any suitable method, and can include physical removal such as by surgery. However, it should be noted that it has been demonstrated that subgingival bacteria remaining after conventional treatments have the potential to re-colonize to pretreatment levels if not property maintained, thus fostering the re-growth of obligate anaerobes. For example, in one known study, oral biofilm was evaluated before and after conventional periodontal therapy. Samples taken before periodontal therapy harbored more bacteria than after therapy. Samples taken after periodontal therapy had the same species as were present before treatment, but in a reduced number both sets of biofilms grew at a similar rate. The treatments as described here can provide for the removal of the subgingival bacteria that remains after conventional periodontal treatments as they have the potential to re-colonize to pretreatment levels if the corrected environment is not otherwise properly maintained.

Following the removal process, a colloidal hydrogen peroxide gel, or suitable substitutes and equivalents, is applied to the sulcus such as by using a periodontal medicament delivery tray, for example sometimes referred to herein as Perio Tray™ treatments. Examples, of such available application methods include Perio Chip, Arestin, Perio Tray/Perio Gel, Atridox, and Actisite. Of course those skilled in the art will recognize that there are other current and future suitable alternatives, each of which is considered to be within the scope of the present disclosure. Additionally, it should be understood that this process may be provided as instructions to a patient for their self-care.

These treatments facilitate healing of the affected tissue by providing or continuing to maintain the modified environment and to continue to prohibit the growth of pathogenic bacteria. In this manner, the gains made in prior processes are maintained and the growth of any additional pathogenic and especially anaerobic bacteria within the gums is suppressed. This application of the colloidal gel, such as hydrogen peroxide gel, to the sulcus and/or periodontal pocket can further inhibit the development of the obligate anaerobic population within the treated environment and can foster healing of the host connective tissue. As one example, a Perio gel at 1.7 percent from Perio Pharma has been evaluated as to efficacy in management of oral periopathogens in an anaerobic environment and is one example of a suitable treatment for this process.

The scope and magnitude of the disease, the depth of the periodontal pocket and the colonization of the pathogenic and especially pathogenic bacteria determine the frequency and duration of treatments. Modifications in the environment render a change in the bacterial flora and changes in the host response, which will result in a modification in the frequency and duration of medicament usage.

The utilization of a periodontal medicament delivery tray such as the Perio Tray™ in this administration of the colloidal hydrogen peroxide gel, or suitable substitutes, can include, but is not limited to, filling at least a portion of a periodontal medicament delivery tray (could be the same or a different one than identified above) with the hydrogen peroxide gel and attaching the tray about the gingival tissue in such a manner as to direct the medicaments to the oral biofilm. Of course it should be understood to those skilled in the art that the administering of the colloidal hydrogen peroxide gel to the gingival tissue can be repeated more than once and site-specific medications can be delivered for optimal control of certain pathogens. For example, the administering can be repeated on a periodic basis. Additionally, the administration can be provided subgingival by the patient several times each day or otherwise to adjust the general or site-specific dosage or frequency of medicament administration as may be directed by a dentist or health care professional, such as may be required in accordance with the diseased status and also changes in the status of the disease as healing occurs.

The method also includes application of a cleaning agent to the gingival tissue, gums and/or the tooth of the affected area for removal of any dead bacterial cells or the protein layer that may be present. This can be any suitable cleaning agent and use any suitable cleaning method. In one embodiment, this includes use of a sonic or ultrasonic cleaning agent using a sonic cleaning device or system that is applied to the affected area generally following the application of a colloidal medicament directly to the sulcus. The inventor hereof has found that the process of cleaning the gingival tissue following the above steps provides for an improved and more effective removal of the protein layer and the bacteria attached to this layer by the sonic cleaning agent. Additionally, this order of processes was found in some embodiments to disrupt the protein layer that improves the effectiveness of the sonic cleaning agent in removing the protein layer. Such removal can be provided before the pathogenic bacteria can repopulate the tooth surface. Additionally, the follow-up cleaning process can create a continued oxygen rich environment, for continued modifying the environment where the facultative anaerobic bacteria and the obligate anaerobes grow. In this manner, the biofilm is modified from one conducive to disease to one that is conducive to the growth of bacteria that can live in harmony with the host, e.g., commensal bacteria.

In some embodiments as described herein, the facilitation of cleaning occurs through a modification of the environment. Oral bacteria are not able to bind to oral structures directly, but require a protein, amino acid layer on which to attach. Initially aerobic bacteria colonize the region, but if the region becomes conducive to the formation of facultative anaerobic bacteria, the region can become anaerobic. One of the initial steps in treatment and cleansing must therefore be a modification of the protein or amino acid layer. This is accomplished through a timed occurrence delivery and the action of colloidal hydrogen peroxide as it permanently modifies the protein layer and by altering the amino acids in a permanent manner (cleaves hyaluronic acid, converts histadine to alanine and asparagine to aspartate) whereby the protein layer or amino acid layer is disrupted and is more easily removed by mechanical or sonic means.

Of course, it should be understood that the cleaning of the gingival tissue can be repeated two or more times and in one embodiment, is at least repeated following each of any repeated administering of the colloidal hydrogen peroxide gel. Such cleaning can be provided by the patient several times each day or otherwise to the frequency as may be directed by a dentist or health care professional. Additionally, such cleaning can be directed or provided as instructions from the medical provider to the patient for self-care.

The protein and amino acid modification alters the substrate such that mechanical and sonic cleaning agent, by way of example, a sonic toothbrush that applies a cleaning agent such as a sonic cleaning agent to the gingival tissue.

There are multiple potential cleaning agents readily available that include dentifrices, mouth rinses, tooth paste, oral irrigants and other commercial products.

It should also be noted that the above processes can first begin with an examination using suitable methods to evaluate the presence and effects of periodontal disease. During such examination process, the requirement of one or more medicament delivery methods is evaluated and their sequence in utilization is determined. For example, in one embodiment, it may be determined that a periodontal medicament delivery tray may be an applicable method for delivery of medicaments for the treatments as described herein. For example, a Perio Tray™ may be the preferred delivery system. In such cases, the fabrication of a tray may be initiated during an early examination and prior to application of the above other processes of the method. This can be at any time prior to the remaining treatment processes. Currently such periodontal medicament delivery trays often take some time to be fabricated, especially if one is not currently available for the patient's use. However, there may be some instances where a periodontal medicament delivery tray may already be available to the patient. In such instances, this portion of the process may be skipped especially as to obtaining the impression and the fabrication of the periodontal medicament delivery tray. At other times, it may be conducive to initiate conventional periodontal treatments; such as scaling and root planning, surgery, laser surgery or localized delivery of antibiotic or antimicrobial agents to the infected area (Arestin, Perio Chip, Atridox, Actisite, etc.)

In some instances where a Perio Tray™ is preferred, this can include fabrication of the periodontal medicament delivery tray 50 such as preparing a female impression of the patient's teeth and adjacent gums that are the affected gums, making a male model of the patient's teeth and adjacent gums from the female impression, and fabricating the tray 50 from the male model. In one embodiment, this also includes forming a raised seal 53 in a location such that a resilient material is formed as a seal against the patient's adjacent gums. The seal 53 is formed with minimal contact to the patient's teeth, but in a manner to direct medications to the source of the infection.

In the situation where a patient is identified as suffering of an obligate anaerobic infection (that is an organism that survives only in the absence of oxygen, e.g., obligate anaerobe), the method provides for the direct application of an aerobic colloid applied directly into the sulcus or periodontal pocket. In a situation where a patient is found to suffer with a specific pathogen dominated disease, direct medications can be delivered to that specific site to assist in controlling the infectious agent. The medicament should be able to readily penetrate the biofilm and biofilm matrix and may contain an aerobic solution, such as a hydrogen peroxide colloid by way of example that is held in the sulcus for a period of time that is long enough to modify the environment from an anaerobic one to an oxygen rich aerobic one, or it may be a more bacteria-specific agent that can optimize microbial control. In a like manner, any medicament can be applied to manage the microbes and provide an environment conducive to health.

Colloidal gels as described herein can include, but are not limited to Perio Gel from Perio Pharma, Peroxyl from Colgate Palmolive, and Carbamide peroxide gel, by way of examples.

The period of time can vary based on the conditions of the periodontal disorder but is generally from about 10 to 15 minutes.

The method of direct application can vary in accordance to the scope and magnitude of the disease, even to the point of microbial-specific medication delivery to specific sites of the infection. Gingivitis treatments usually can be rendered from one to three times a day and long-term maintenance can be obtained with daily or twice daily applications. Periodontitis treatments can be rendered from two to six times a day, modified as healing occurs and maintained with long-term usage of two or more times a day as determined by the patient's conditions and healing. Any region that requires site-specific treatment can be administered as the micro-organisms are recognized to require specific considerations.

The various methods of direct application of this medicament can include, but is not limited to, oral rinses, application through brushing or flossing, direct application and through usage of the Perio Tray™ system and special microbial-specific medications. Oral rinses are not generally deliverable into the periodontal pocket as rinses are unable to overcome crevicular flow. Similarly, brushing and flossing do not typically penetrate greater than 3 mm into the periodontal pocket and even then crevicular flow dilutes the medicaments. In addition, the bacteria are so small and reproduce so rapidly that mechanical removal alone has proven ineffective in controlling them. Likewise, direct medicament applications into the periodontal pocket are unable to maintain a sufficient amount of medicament over an extended period of time and are not renewable to alter the environment and maintain a modified environment sufficient for health and healing. As such, a periodontal medicament delivery tray such as the Perio Tray™ system has been found to provide for direct application of the medicament in many situations and applications. This can encompass general medicament delivery or site-specific micro-organism specific medicaments.

In some embodiments, the direct application of the aerobic colloid a periodontal medicament delivery tray such as the Perio Tray™ can create an oxygen rich environment that kills the obligate anaerobes contained therein and kills the facultative anaerobes (a facultative parasite can live independently of its usual host as they can live off the waste products of other bacteria) as well as aerobic bacteria in the associated biofilm. This includes killing facultative anaerobes including bacteria that can live in both aerobic and anaerobic environments. By killing the facultative anaerobes, they are prevented from modifying the environment to one where the most virulent obligate anaerobes are able to function. As such, this process that includes killing these facultative anaerobes in the biofilm in addition to the then present obligate anaerobes (including those that cause decay) can provide for inhibiting the future growth of obligate anaerobes in addition to killing those currently present. It would also be possible to introduce specific beneficial bacteria into the regions as healing occurs to compete with the pathogenic bacteria and promote healing and a healthy environment.

The medicament, such as the colloidal hydrogen peroxide gel, by way of example, can in some situations be limited to treatments where there is an acute infection. As such, the administering of the colloidal hydrogen peroxide gel can be provided in the acute phase treatments to address the virulent pathogens and to change the environment from one conducive of virulent pathogen development to one that is not conducive thereof. However, the administering process may not be applied in some embodiments of the method. This particular process step can be applied following examination and prior to the other steps of the method, such as, for example, during and/or in parallel to the fabrication or procurement of a suitable periodontal medicament delivery tray for the particular patient. It is also understood that site-specific micro-organism-specific medications could be used as deemed appropriate by the health care provider.

It should also be understood that the administering process can be practiced once or can be repeated two or more times as may be needed or desired such as to modify the environment to one that is conducive to the growth of more commensal bacteria that are not pathogenic, e.g., an oxygen rich aerobic environment. It is also possible to introduce commensal bacteria into the sulcus or periodontal pocket by direct application means. It should also be understood that such direct application of a medicament can be provided by the health care provider or by the patient several times each day or otherwise adjusted to the frequency and length as may be directed by a dentist or health care professional.

As described herein, a periodontal medicament delivery tray may be any suitable tray for direct applicant of a medicament about the teeth and gums. One example, of such is the Perio Tray™ as described in the U.S. Pat. No. 6,966,773, as issued to the inventor hereof. As described herein, such periodontal delivery trays, or variations thereof, can be worn by the patient for the purpose of controlling the oral periopathogens that are associated with specific systemic disease factors and conditions.

The methods and systems as described herein address the pathogens in a synergistic approach that provides steps that collectively have an unknown or unexpected benefit over the expected results of each of the separate or individual steps.

Literature in the medical and dental journals demonstrate that being able to control oral periopathogens have effects on systemic situations. Various embodiments of the present systems and methods can provide for the control of oral periopathogens that have effects on systemic situations, for example, scaling and root planning decrease C-reactive protein and lower patient lipid levels, decreases patients glycosylated hemoglobin and decreases the incidence of premature and low birth weight babies.

In a study by the inventor hereof, patients treated with the methods and systems as described herein, resulted in a significant reduction in their CRP levels. In fact, the inventor has found that 29 of 32 patients were successful at maintaining these significantly reduced CRP levels and such levels were normal for up to one year following treatment. It should be noted that of the patients that had elevated levels, each of the patients had a systemic reason (infection, gastroenteritis, etc.) for the elevation. The pilot program only included treatment to control the periopathogens and as such was successful at documenting the decrease in the systemic CRP involvement (inflammation, injury or infection).

Additionally, the inventor hereof has also documented using a scanning electron microscopy that the periopathogens can be reduced by 99.98% within 12 to 17 days of the start of the treatment as described herein. These results can continue to control the periopathogens long-term in patients who use of the methods as described herein.

Patient's C-reactive protein systemic levels decreased when treated with the system and oral methods as described in this present disclosure. It is also expected that other systemic markers changes will result from the resulting control of the periopathogens.

One embodiment of a pilot program as described herein had been held wherein the C-reactive protein changes in patients have been measured. The results of this pilot program resulted in 29 of 32 patients having their C-reactive protein levels return to normal. C-reactive protein is associated in the medical literature with cardiovascular problems, Alzheimer's disease, Type II diabetes and pre-term and low birth weight babies and other systemic inflammatory changes.

This can provide the benefit over the prior practices and methods as some embodiments of the current method can provide for controlling one of the causes of systemic inflammation, thereby controlling systemic improvements in a patient. In addition, in various embodiments the control of the bacteria that causes decay can decrease the incidence of new or recurrent decay and site-specific medication applications are possible when needed.

As used herein, a biofilm is intended to refer to any complex structure of a mixed bacterial colony adhering to surfaces that are regularly in contact with oral fluids, consisting of colonies of bacteria and usually other microorganisms such as yeasts, fungi, and protozoa that secrete a mucilaginous protective coating in which they are encased. These biofilms can form on solid or liquid surfaces as well as on soft tissue in living organisms, and are typically resistant to conventional methods of disinfection. Dental plaque is an example of a biofilm. Biofilms are generally pathogenic in the body, causing such diseases as cystic fibrosis and otitis media.

An anaerobe as used herein is an organism, such as a bacterium, is one that can live in the absence of atmospheric oxygen, e.g., does not require air or free oxygen to live. Pathogenic bacteria as used herein defines any microorganisms that reside in a parasitic or harmful manner and causes infectious, injurious, inflammatory or other deleterious effects on the host. Additionally, while bacteria such as anaerobic bacteria is described in this disclosure, such reference is by way of exemplary embodiment. It should be understood that such references to bacteria can similar include or alternatively apply to micro-organisms, wherein micro-organisms are fully within the scope of the present disclosure.

As used herein, commensal refers to a symbiotic relationship in which one species is benefited while the other is unaffected or an organism participating in a symbiotic relationship in which one species derives some benefit while the other is unaffected.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. A method of treating systemic disease related to oral biofilms having a facultative anaerobic bacteria pathogen present within a subgingival biofilm associated with the oral biofilm wherein the subgingival biofilm has a protein layer and an amino acid comprising:
    providing a periodontal medicament delivery tray having a seal against the patient's adjacent gums containing the oral biofilms having the systemic disease, said seal formed so as to have no contact with teeth;
    applying an antimicrobial agent to a subgingival portion of a tooth and a gingival tissue surrounding the tooth by filling at least a portion of the periodontal medicament delivery tray with the antimicrobial agent and attaching the delivery tray about the gingival tissue; the applying of the antimicrobial agent penetrating the subgingival biofilm and the gingival tissue associated with such subgingival biofilm wherein the applying is repeated a plurality of times until an environment associated with the subgingival biofilm is altered from anaerobic to aerobic, killing the facultative bacteria pathogen, modifying the protein layer, and altering the amino acid associated with the subgingival biofilm to cleave hyaluronic acid, convert histadine to alanine and asparagine to aspartate;
    surgically removing the remaining and imbedded facultative anaerobic bacteria from the gingival tissue following the applying of the antimicrobial agent that obtains the aerobic environment associated with the subgingival biofilm, the killing of the facultative bacteria pathogen, the modification of the protein layer and the altering of the amino acid;
    administering a colloidal hydrogen peroxide gel to a periodontal pocket or a sulcus associated with the gingival tissue, the subgingival biofilm, and the gingival tissue in conjunction with or following the surgically removing of at least a portion of the imbedded anaerobic bacteria to chemically remove a further portion of the imbedded anaerobic bacteria not removed during the prior surgical removing process, wherein administering includes filling at least a portion of the periodontal medicament delivery tray with the colloidal hydrogen peroxide gel and attaching the delivery tray about the gingival tissue associated with the periodontal pocket;
    repeating the administering of the colloidal hydrogen peroxide gel on a periodic basis for maintaining an environment conducive to only aerobic bacteria; and
    cleaning the gingival tissue with a cleaning agent directly following each administering of the colloidal hydrogen peroxide gel.

2. The method of claim 1, further comprising performing an evaluation examination of the patient, wherein providing the periodontal medicament delivery tray is initiated during the performing of the evaluation examination; and preparing a periodontal medicament delivery tray wherein preparing the periodontal medicament delivery tray includes fabricating the delivery tray including preparing a female impression of a patient's teeth and adjacent gums associated with the oral biofilms being treated, making a male model of the patient's teeth and adjacent gums from the female impression and forming an indented feature on the male model about the gum line set apart from teeth, and having the delivery tray fabricated from the male model with a raised seal in a location of the indented feature on the male model, the raised seal being formed from a resilient material forming a seal against the patient's adjacent gums when the periodontal medicament delivery tray is applied thereto.

3. The method of claim 2, further comprising:
    selecting the antimicrobial agent that is capable of readily penetrating the subgingival biofilm and a biofilm matrix associated with the oral biofilm responsive to the evaluation examination.

4. The method of claim 1, further comprising:
    selecting the antimicrobial agent to be applied for each of the plurality of times of applying an antimicrobial agent, wherein the selecting is from a plurality of antimicrobial agents, wherein selecting includes prior to at least one of the one or more times of applying the antimicrobial agent, determining a bacteria present in the subgingival biofilm or the gingival tissue associated with the subgingival biofilm.

5. The method of claim 1 wherein the process of applying the antimicrobial agent is applying an oxygenating agent.

6. The method of claim 1 wherein the applied antimicrobial agent is selected from the group consisting of Perio gel, hydrogen peroxide, Peroxyl, carbamide peroxide, whitening and bleaching gels.

7. The method of claim 1 wherein the applying of the antimicrobial agent is on a periodic basis.

8. The method of claim 1 wherein the process of surgically removing imbedded anaerobic bacteria includes a process selected from the group consisting of electro-surgery, scaling, and root planning laser surgery, and cold-steel surgery.

9. The method of claim 1 wherein surgically removing the imbedded anaerobic bacteria includes removing the facultative anaerobic bacteria from a periodontal pocket located in close proximity to a capillary bed of the gingival tissue.

10. The method of claim 1, further comprising repeating the cleaning of the gingival tissue with a cleaning agent directly following each repeated administering of the colloidal hydrogen peroxide gel.

11. The method of claim 1 wherein the cleaning includes using at least one of a mechanical and a sonic toothbrush for applying a cleaning agent to the gingival tissue.

12. The method of claim 1 wherein the cleaning agent is applied to a sulcus of the gingival tissue by using the delivery tray adapted for establishing an environment of health and healing and reduces the environment of disease and infection, wherein the process of cleaning includes using a sonic cleaning device with the cleaning agent that is suitable for use with said sonic cleaning device.

13. The method of claim 1, in addition to the applying of the antimicrobial agent the plurality of times to the subgingival portion of the tooth and the gingival tissue surrounding the tooth to obtain the aerobic environment and in addition to the administering of the colloidal hydrogen peroxide gel to the periodontal pocket associated with the subgingival biofilm, further comprising applying an aerobic colloid directly to a sulcus area associated with the tooth and gingival tissue being treated following the applying that obtains the aerobic environment, the removal of the imbedded anaerobic bacteria by the surgical removing and the administering of the colloidal hydrogen peroxide to the periodontal pocket and the cleaning, wherein the applying the aerobic colloid directly to the sulcus area inhibits the future growth of obligate anaerobes on the tooth and gingival tissue, wherein the aerobic colloid is a hydrogen peroxide colloid or a colloid selected from the group of oxygenation medicaments consisting of hydrogen, carbamide peroxide or other agents commercially available.

14. The method of claim 1, further comprising, following the applying of the antimicrobial agent to obtain the aerobic environment, the surgically removing the portion of the imbedded anaerobic bacteria from the gingival tissue, and the administering of the colloidal hydrogen peroxide to the periodontal pocket, directly applying a commensal bacteria into the sulcus or a periodontal pocket associated with the gingival tissue to re-colonization the sulcus or the periodontal pocket with the commensal non-harmful bacteria.

15. The method of claim 1, further comprising providing instructions to a patient including the process of administering and cleaning for enabling the patient for performing the administering and the cleaning.

16. A method of treating systemic disease related to oral biofilms having a facultative anaerobic bacteria pathogen present within a subgingival biofilm associated with the oral biofilm wherein the subgingival biofilm has a protein layer and an amino acid comprising:
  providing a periodontal medicament delivery tray having a seal against the patient's adjacent gums containing the oral biofilms having the systemic disease, said seal formed so as to have no contact with teeth;
  applying an antimicrobial agent to a subgingival portion of a tooth and a gingival tissue surrounding the tooth by filling at least a portion of the periodontal medicament delivery tray with the antimicrobial agent and attaching the delivery tray about the gingival tissue, the applying of the antimicrobial agent penetrating the subgingival biofilm and the gingival tissue associated with such subgingival biofilm on a periodic basis, said applying includes filling at least a portion of the periodontal medicament delivery tray with the antimicrobial agent and attaching the tray about the gingival tissue, the applying being repeated until an environment associated with the subgingival biofilm is altered from anaerobic to aerobic, the facultative bacteria pathogen is killed, the protein layer is modified and the amino acid is altered to cleave hyaluronic acid, convert histadine to alanine and asparagine to aspartate;
  surgically removing the remaining and imbedded facultative anaerobic bacteria from the gingival tissue following the applying of the antimicrobial agent that obtains the aerobic environment associated with the subgingival biofilm, the killing of the facultative bacteria pathogen, the modification of the protein layer, and the altering of the amino acid; and
  providing instructions to a patient including instructions for filling at least a portion of the periodontal medicament delivery tray with the colloidal hydrogen peroxide gel and attaching the delivery tray about the gingival tissue associated with the periodontal pocket, repeatedly administering the colloidal hydrogen peroxide gel to the periodontal pocket associated with the subgingival biofilm and the gingival tissue in conjunction with or following the surgically removing of at least a portion of the imbedded anaerobic bacteria to chemically remove a further portion of the imbedded anaerobic bacteria not removed using the prior surgical removing process, and following each administering cleaning the gingival tissue with a cleaning agent directly following the administering of the colloidal hydrogen peroxide gel.

17. The method of claim 16, further comprising:
  selecting the antimicrobial agent to be applied for each application of the applying step from among a plurality of antimicrobial agents, wherein selecting includes determining a bacteria present in the subgingival biofilm or the gingival tissue associated with the subgingival biofilm.

18. The method of claim 17, further comprising, following the process of determining and prior to the applying, selecting the antimicrobial agent that is capable of readily penetrating the subgingival biofilm and a biofilm matrix associated with the oral biofilm.

19. The method of claim 16, further comprising, following the applying of the antimicrobial agent to obtain the aerobic environment, the surgically removing the facultative anaerobic bacteria from the gingival tissue, and the repeated administering of the colloidal hydrogen peroxide to the periodontal pocket,
  directly applying a commensal bacteria into the sulcus or a periodontal pocket associated with the gingival tissue to re-colonization the sulcus or the periodontal pocket with the commensal non-harmful bacteria.

20. The method of claim 16 wherein the step of providing the periodontal medicament delivery tray is initiated during an evaluation examination and the step of providing the periodontal medicament delivery tray includes preparing the periodontal medicament delivery tray by fabricating the periodontal medicament delivery tray using the steps of preparing a female impression of a patient's teeth and adjacent gums associated with the oral biofilms being treated, making a male model of the patient's teeth and adjacent gums from the female impression and forming an indented feature on the male model about the gum line set apart from teeth, and having the delivery tray fabricated from the male model with a raised seal in a location of the indented feature on the male model, the raised seal being composed of a resilient material and forming a seal against the patient's adjacent gums when the periodontal medicament delivery tray is applied thereto.

* * * * *